United States Patent
Hutchenson et al.

(10) Patent No.: US 7,166,727 B2
(45) Date of Patent: *Jan. 23, 2007

(54) SUPERCRITICAL FLUID PHASE SYNTHESIS OF METHYLENE LACTONES USING NOVEL GRAFTED CATALYST

(75) Inventors: Keith W. Hutchenson, Lincoln University, PA (US); Kostantinos Kourtakis, Media, PA (US); Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/168,647

(22) Filed: Jun. 28, 2005

(65) Prior Publication Data

US 2006/0025605 A1  Feb. 2, 2006

Related U.S. Application Data

(60) Provisional application No. 60/591,517, filed on Jul. 27, 2004.

(51) Int. Cl.
| | |
|---|---|
| C07D 307/02 | (2006.01) |
| C07D 407/00 | (2006.01) |
| C07D 305/12 | (2006.01) |
| C07D 307/00 | (2006.01) |

(52) U.S. Cl. ........................................ 549/295; 549/326
(58) Field of Classification Search ................ 549/295, 549/326
See application file for complete search history.

(56) References Cited

U.S. PATENT DOCUMENTS

| 6,313,318 B1 | 11/2001 | Coulson et al. | |
|---|---|---|---|
| 2003/0166949 A1 | 9/2003 | Manzer et al. | |
| 2006/0025607 A1* | 2/2006 | Hutchenson et al. | 549/263 |
| 2006/0025608 A1* | 2/2006 | Hutchenson et al. | 549/263 |
| 2006/0025610 A1* | 2/2006 | Hutchenson et al. | 549/263 |
| 2006/0025611 A1* | 2/2006 | Hutchenson et al. | 549/263 |
| 2006/0025612 A1* | 2/2006 | Hutchenson et al. | 549/263 |

FOREIGN PATENT DOCUMENTS

| JP | 10298172 | * 11/1998 |
|---|---|---|
| WO | WO 03/057683 | 7/2003 |

OTHER PUBLICATIONS

Mechanical translation of JP 10298172, paragraph 27-33, May 12, 2006.*
K. W. Hutchenson, Organic Chemical Reactions and Catalysis in Supercritical Fluid Media, Supercritical Fluid Technology in Materials Science and Engineering, Y. P. Sun (Ed.), Marcel Dekker; New York 2002, p. 87-187.
Kirk-Othmer Encyclopedia of Chem. Technology, 4th Ed., vol. 23, p. 452-477.
E. P. Barret, L. G. Joyner and P. P. Halenda, J. Amer. Chem. Soc., 73, 373, (1951).

* cited by examiner

Primary Examiner—Margaret D. Seaman
Assistant Examiner—Niloofar Rahmani
(74) Attorney, Agent, or Firm—Gerald E Deitch

(57) ABSTRACT

Process for converting certain lactones to their alpha-methylene substituted forms in a supercritical or near-critical fluid phase reaction using a novel grafted catalyst that not only exhibits high initial activity (conversion), but also maintains a high level of activity with time on stream.

9 Claims, No Drawings

SUPERCRITICAL FLUID PHASE SYNTHESIS OF METHYLENE LACTONES USING NOVEL GRAFTED CATALYST

CROSS-REFERENCE TO RELATED APPLICATION

This application claims priority under 35 U.S.C. §119 from U.S. Provisional Application Ser. No. 60/591,517, filed Jul. 27, 2004.

FIELD OF INVENTION

The invention pertains to a method of producing unsubstituted and substituted alpha-methylene lactones from reaction of starting lactones with formaldehyde in a supercritical or near-critical fluid phase in the presence of a novel grafted catalyst.

BACKGROUND

Alpha-methylene-gamma-butyrolactone and methyl alpha-methylene-gamma-butyrolactone are useful monomers in the preparation of both homopolymers and copolymers. In addition, the alpha-methylene-gamma-butyrolactone group is an important structural feature of many sesquiterpenes of biological importance.

Current ways of making alpha-methylene-gamma-butyrolactone monomer are unattractive because of low yields, byproducts formation and/or expensive starting materials.

In particular, U.S. Pat. No. 6,313,318 describes a method for converting certain starting lactones to alpha-methylene substituted lactones using a so-called basic catalyst that is made by treating silica with an inorganic salt of Ba, Mg, K, Cd, Rb, Na, Li, Sr, and La. A problem inherent in the method is that there is a significant decrease in the conversion of the starting lactone to the alpha-methylene product with time on stream (TOS).

US 2003-0166949 A1 describes a method for converting certain starting lactones to alpha-methylenelactones in a supercritical fluid (SCF) phase using a heterogeneous so-called basic catalyst that can be selected from the Group I, Group II, and Lanthanide Group oxides, hydroxides, carbonates, hydrogen carbonates, silicates, oxalates, carboxylates, acetates and phosphates, and mixtures thereof, any of which may be supported or unsupported. The basic catalyst may include additives and promoters to enhance catalyst efficiency. The method involves a reaction between the starting lactone and formaldehyde and may be carried out in a batch or continuous mode. The process can be run in either a single homogeneous phase over the catalyst, or the reactants and SCF may be in two different phases over the catalyst. The temperature of the reaction can range from about 70° C. to about 400° C., with a preferred range of about 100° C. to about 350° C. A more preferred range is about 200° C. to about 350° C. Pressure ranges are those required to achieve the supercritical or near-critical state under a given set of reaction conditions. The pressure of the reaction can range from about 5 to about 60 MPa, with a preferred range of about 15 to about 40 MPa.

One important measure of reactor performance that is a strong function of the catalyst activity is termed the "reactor productivity," which can be expressed as the mass of product produced per mass of catalyst per unit of time. High and sustained reactor productivity is desired for a manufacturing process to improve economic viability. In addition, high catalyst activity (reactant conversion) is desirable, in general, to minimize additional processing required to separate the product from unconverted reactants. Although this performance parameter was not explicitly shown in the above-cited patent publication for the examples shown therein, the reactor productivity can be estimated from the data provided. Table 1 shows the variation in both catalyst activity (GVL conversion) and reactor productivity for the various examples conducted in continuous reactors. These data illustrate that problems inherent in the method include maximum sustained reactor productivities on the order of only 0.7 gram MeMBL/gram catalyst-hour and an undesirable decrease in activity with time on stream.

TABLE 1

Reactor Productivity Estimates for Reference US 2003-0166949A1

| US 2003-0166949A1 Example No. | Catalyst Composition | WHSV (g GVL/ g cat.-h) | TOS (h) | GVL Conversion (%) | Calculated Reactor Productivity* (g MeMBL/ g cat.-h) |
|---|---|---|---|---|---|
| 15 | K2CO3 | 0.22 | — | 77.1 | 0.19 |
| 16 | K2CO3 | 0.13 | 0.84 | 32.9 | 0.05 |
|  |  |  | 1.09 | 34.2 | 0.05 |
|  |  |  | 1.93 | 33.3 | 0.05 |
|  |  |  | 2.46 | 38.6 | 0.06 |
|  |  |  | 3.00 | 40.2 | 0.06 |
| 17 | 20% K/SiO2 | 0.7 | — | 64.9 | 0.51 |
| 18 | 20% Rb/SiO2 | 0.7 | — | 78.4 | 0.61 |
| 19 | 20% Cs/SiO2 | 0.7 | — | 88.8 | 0.70 |
| 20 | 20% Cs/SiO2 | 0.7 | — | 69.2 | 0.54 |
| 21 | 20% Ca/SiO2 | 0.7 | — | 8.0 | 0.06 |
| 22 | 20% Ba/SiO2 | 0.7 | — | 31.5 | 0.25 |
| 23 | 20% CSiO2 | 0.4 | 1.25 | 89.9 | 0.40 |
|  |  |  | 1.75 | 88.5 | 0.40 |
|  |  |  | 2.25 | 86.2 | 0.39 |
|  |  |  | 2.75 | 83.8 | 0.38 |
|  |  |  | 3.00 | 82.3 | 0.37 |
| 24 | 20% Cs/SiO2 | 0.7 | 1.45 | 94.9 | 0.74 |
|  |  |  | 1.95 | 90.3 | 0.71 |
|  |  |  | 2.45 | 88.7 | 0.70 |
|  |  |  | 2.95 | 86.0 | 0.67 |
|  |  |  | 3.20 | 84.9 | 0.67 |
| 25 | 20% Rb/SiO2 | 0.7 | 1.30 | 94.1 | 0.74 |
|  |  |  | 1.80 | 92.8 | 0.73 |
|  |  |  | 2.30 | 93.5 | 0.73 |
|  |  |  | 2.80 | 94.6 | 0.74 |
|  |  |  | 3.30 | 95.3 | 0.75 |
|  |  |  | 4.10 | 94.9 | 0.74 |
| 26 | 20% Rb/SiO2 | 2.5 | 0.80 | 72.8 | 2.04 |
|  |  |  | 1.00 | 53.8 | 1.51 |
|  |  |  | 1.50 | 37.1 | 1.04 |
|  |  |  | 2.00 | 29.9 | 0.84 |
|  |  |  | 2.50 | 27.2 | 0.76 |
|  |  |  | 3.00 | 25.9 | 0.72 |
|  |  |  | 3.50 | 24.8 | 0.69 |
|  |  |  | 4.00 | 25.2 | 0.71 |
|  |  |  | 5.00 | 26.3 | 0.74 |
|  |  |  | 5.50 | 26.0 | 0.73 |
| 27 | 20% Cs/SiO2 | 0.7 | 1.20 | 30.9 | 0.24 |
|  |  |  | 2.00 | 30.6 | 0.24 |
|  |  |  | 2.50 | 27.2 | 0.21 |
|  |  |  | 3.00 | 26.0 | 0.20 |
|  |  |  | 3.50 | 23.9 | 0.19 |
|  |  |  | 4.00 | 22.1 | 0.17 |
| 28 | 20% Rb/SiO2 | 2.5 | 0.90 | 17.9 | 0.50 |
|  |  |  | 1.20 | 5.1 | 0.14 |
|  |  |  | 1.60 | 0.8 | 0.02 |
|  |  |  | 1.90 | 0.6 | 0.02 |
|  |  |  | 2.40 | 0.3 | 0.01 |

TABLE 1-continued

Reactor Productivity Estimates
for Reference US 2003-0166949A1

| US 2003-0166949A1 Example No. | Catalyst Composition | WHSV (g GVL/ g cat.-h) | TOS (h) | GVL Conversion (%) | Calculated Reactor Productivity* (g MeMBL/ g cat.-h) |
|---|---|---|---|---|---|
| 29 | 15% Cs/SiO2 | 0.7 | 1.9 | 95.4 | 0.75 |
|    |             |     | 2.4 | 93.8 | 0.74 |
|    |             |     | 2.9 | 90.7 | 0.71 |
|    |             |     | 3.9 | 89.8 | 0.70 |
|    | (1st Regen.) | 0.7 | 1.90 | 62.4 | 0.49 |
|    |             |     | 2.50 | 57.5 | 0.45 |
|    |             |     | 3.00 | 55.2 | 0.43 |
|    | (2nd Regen.) | 0.7 | 1.80 | 63.4 | 0.50 |
|    |             |     | 2.50 | 55.7 | 0.44 |
|    |             |     | 3.00 | 54.1 | 0.42 |
| 30 | 15% Cs/SiO2 | 1.7 | — | 4.8 | 0.09 |
| 31 | 20% Rb/SiO2 | 1.1 | — | 28.7 | 0.35 |

*Productivity estimated as product of WHSV, GVL Conversion, and Ratio of Molecular Weights of MeMBL/GVL (112.1/100.12) assuming 100% Selectivity to MeMBL.

It would be advantageous, therefore, to have a lactone conversion process that not only exhibits high initial activity (conversion), but also provides high reactor productivity (mass of product per mass of catalyst per unit of time) and sustained maintenance of a high level of activity and productivity with time on stream.

SUMMARY OF THE INVENTION

This need is met by the present invention, which, in its first aspect, is a process for preparing a reaction product comprising an alpha-methylene lactone of the Formula II, said process comprising combining a lactone of the Formula I with formaldehyde derived from a formaldehyde source and a solvent to produce a reaction mixture,

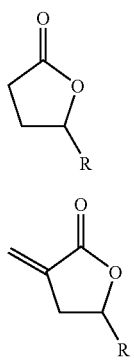

wherein R is selected from the group consisting of hydrogen, methyl, ethyl, and straight or branched $C_3$–$C_5$ alkyl;

at a temperature and pressure sufficient to cause the reaction mixture to exist as a supercritical or near-critical fluid; said temperature being sufficient to cause the formation of said alpha-methylene lactone of Formula II; said reaction mixture being in the presence of a grafted catalyst;

said catalyst made by (or obtainable by) a process comprising:

(a) contacting (i) porous silica, optionally containing at least one first element selected from the group consisting of aluminum, zirconium, and titanium, said silica having a pore volume of at least 0.4 cc/g attributable to pores having pore diameters between 65 and 3200 Angstroms, with (ii) a solution comprising a solvent and an organic compound of at least one second element selected from the group consisting of potassium, cesium and rubidium;

(b) drying the product of step (a) to remove at least a portion of said solvent;

(c) heating the product of step (b) to a temperature in the range of 350° C. to 550° C. to produce a catalyst precursor;

(d) flushing at a preselected flow rate an oxygen-containing gas over said catalyst precursor either during step (c), or after step (c) while the temperature is still in the range of 350° C. to 550° C. to produce a catalyst candidate in which the at least one second element is present in said catalyst candidate in an amount from about 0.1% to about 40% by weight of the combined weight of the catalyst candidate and the second element;

(e) determining by porosimetry whether said catalyst candidate has a pore volume of at least about 0.3 cubic centimeters per gram of catalyst attributable to pores having a diameter between 65 and 3200 Angstroms; and (f) if said catalyst candidate does not have a pore volume of at least about 0.3 cubic centimeters per gram of catalyst attributable to pores having a diameter between 65 and 3200 Angstroms, repeating, optionally more than once, steps (a) through (e) using in step (d) flow rates successively greater than said preselected flow rate until the catalyst candidate has a pore volume of at least about 0.3 cubic centimeters per gram of catalyst attributable to pores having a diameter between 65 and 3200 Angstroms;

(g) contacting the material produced in step (f) with a second solution of zirconium, aluminum or titanium alkoxides dissolved in a second solvent, said alkoxides containing from one to 20 carbon atoms;

(h) filtering the material of step (g);

(i) drying the product of step (h) to remove at least a portion of said second solvent;

(j) heating the product of step (b) to a temperature in the range of 350° C. to 550° C.;

(k) flushing at a preselected flow rate an oxygen-containing gas over said catalyst precursor either during step (j), or after step (j) while the temperature is still in the range of 350° C. to 550° C. to produce the grafted catalyst.

In its second aspect, the present invention is the grafted catalyst made by the process recited above.

The use of such a catalyst in the conversion of lactones of the Formula I to those of Formula II leads not only to high initial activity (conversion), but also to the maintenance of a high level of activity with time on stream.

DETAILED DESCRIPTION OF THE INVENTION

The following terms generally are abbreviated as follows:
"alpha-methylene-gamma-butyrolactone" is abbreviated MBL;
"gamma-butyrolactone" is abbreviated GBL;
"gamma-valerolactone" is abbreviated GVL;

"alpha-methylene-gamma-valerolactone" is abbreviated MVL;
gamma-methyl alpha methylene gamma butyrolactone is abbreviated MeMBL;
"time on stream" is sometimes abbreviated TOS;
"cubic centimeters" is abbreviated as cc or cm³;
"mass spectroscopy" is abbreviated MS;
"gas chromatography" is abbreviated GC;
"supercritical fluid" is abbreviated SCF; and
"weight hour space velocity" is abbreviated WHSV.

The process of the present invention concerns a supercritical or near-critical fluid phase methylenation of lactones of Formula I to yield alpha-methylene lactones of Formula II.

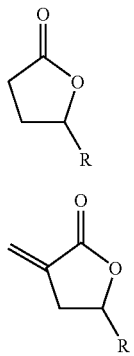

I

II

Specifically, lactone of Formula I is reacted with formaldehyde to give a reaction product comprising alpha methylene lactones of Formula II. The substituent —R group is selected from the group consisting of hydrogen, methyl, ethyl, and straight or branched $C_3$–$C_5$ alkyl. Also produced is an internal isomer of the lactone of Formula II, represented by Formula III, below.

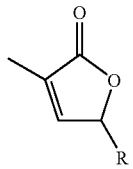

III

In a preferred embodiment the lactone of Formula I is gamma-butyrolactone (R is H) and the alpha-methylene lactone of Formula II is alpha-methylene-gamma-butyrolactone. In a most preferred embodiment the lactone of Formula I is gamma-valerolactone (R is CH₃) and the alpha-methylene lactone of Formula II is alpha-methylene-gamma-valerolactone.

The process of the present invention is conducted at reaction conditions to achieve a supercritical or near-critical fluid state. The temperature is in the range of from about 70° C. to about 400° C. A temperature in the range of from about 100° C. to about 350° C. is preferred. A temperature in the range of from about 200° C. to about 350° C. is most preferred. The pressure is in the range of from about 5 MPa to about 60 MPa, with a preferred range of from about 15 MPa to about 40 MPa. The catalyst contact time and temperature can be selected to achieve desired yields and selectivities. Contact time can be manipulated by increasing or decreasing flow rates over the catalyst.

The lactones of Formula I, formaldehyde, and the solvent can be in a homogeneous supercritical fluid phase. Alternatively the lactones of Formula I, formaldehyde, and solvent may be in two different phases (one supercritical) over the solid catalyst.

The formaldehyde may be supplied to the reaction in the form of an aqueous solution (formalin), anhydrous formaldehyde, formaldehyde hemiacetal, a low molecular weight polyformaldehyde (paraformaldehyde), or formaldehyde trimer (trioxane). The use of paraformaldehyde, trioxane, or anhydrous formaldehyde is preferred since this reduces the need to remove water from the process. Hemiacetals work effectively, but require separate steps to release the formaldehyde from the alcohol and to recover and recycle the alcohol.

The catalyst used in the present invention comprises silicon and oxygen that form a matrix (or support) for a catalytic element. The catalytic element is at least one element selected from the group consisting of potassium, cesium and rubidium. The catalytic element is first deposited on or dispersed within the matrix by contacting the matrix with a solution of an organic compound of at least one of these elements. The matrix comprising silicon and oxygen can optionally comprise at least one compound comprising an element selected from the group consisting of titanium, aluminum and zirconium. The catalytic element should constitute from about 0.1% to about 40% by weight of the combined weight of the pre-grafted catalyst and the added catalytic element (as opposed to the entire compound of which the element is a part).

The catalyst onto which the aluminum, titanium or zirconium alkoxides are grafted must be porous and have a pore-size distribution such that those pores having a diameter between 65 and 3200 Angstroms provide a pore volume of at least about 0.3 cubic centimeters per gram of the catalyst.

In some cases, reaction conditions may result in a decrease of catalyst efficiency. In these situations it may be useful to periodically reactivate the catalyst. For example, contacting the present catalysts, when activity drops below an acceptable level, with oxygen at elevated temperatures has the effect of reactivating the catalyst. Contact temperatures with oxygen may range from about 225° C. to about 500° C., with temperatures of about 250° C. to about 425° C. being preferred.

Selectivities and yields of product may be influenced by the total contact time with the catalyst. As stated previously, yields and selectivities may be increased by adjusting gas and liquid flow rates.

The present method exploits several advantages of using a supercritical fluid (SCF) as the reaction solvent. SCFs are attractive media for conducting chemical transformations, primarily because the solvent and transport properties of a single solution, including the density, can be varied appreciably and continuously with relatively minor changes in temperature or pressure. The density variation in a SCF also influences the chemical potential of solutes and thus reaction rates and equilibrium constants. Thus, the solvent environment can be optimized for a specific reaction application by tuning the various density-dependent fluid properties. For a discussion of advantages and applications of supercritical fluid media for chemistry and catalysis, see Hutchenson, K. W., "Organic Chemical Reactions and Catalysis in Supercritical Fluid Media," in *Supercritical Fluid Technology in*

*Materials Science and Engineering*, Y. -P. Sun (ed.), Marcel Dekker: New York (2002), pp. 87–187.

A fluid is in the SCF state when the system temperature and pressure exceed the corresponding critical point values defined by the critical temperature ($T_c$) and pressure ($P_c$). For pure substances, the critical temperature and pressure are the highest at which vapor and liquid phases can coexist. Above the critical temperature, a liquid does not form for a pure substance, regardless of the applied pressure. Similarly, the critical pressure and critical molar volume are defined at this critical temperature corresponding to the state at which the vapor and liquid phases merge. Similarly, although more complex for multicomponent mixtures, the mixture critical state is identified as the condition at which the properties of coexisting vapor and liquid phases become indistinguishable. For a discussion of supercritical fluids, see *Kirk-Othmer Encycl. of Chem. Technology*, $4^{th}$ Ed., Vol. 23, pg. 452–477.

In addition to typical factors such as chemical inertness, cost, toxicity, etc., the critical temperature must be considered when selecting a potential solvent for conducting chemical transformations in the SCF regime. For practical applications, thermal and catalytic chemical reactions can only be conducted in a relatively narrow temperature range. Lower temperatures result in unacceptable reaction rates, and higher temperatures can result in significant selectivity and yield losses as well as catalyst deactivation. To obtain practical solvent densities and the corresponding density-dependent properties, this temperature optimization must be balanced against a general desire to operate in the vicinity of the mixture critical point of the reaction system to fully exploit the potential advantages afforded by SCF operation. The phase behavior of the reaction mixture, which is strongly influenced by the solvent critical temperature, is fundamentally important in defining this operating window, so one must select a solvent to provide the desired phase behavior. The phase behavior of SCF systems can also be manipulated to control the number and composition of coexisting phases, thus controlling both reaction effects as well as the separation of products or homogeneous catalysts from the reaction mixture.

In practice, a number of desirable properties characteristic of the SCF state are also realized in the expanded liquid region that exists at temperatures and pressures slightly below this critical point. Hence, for the purposes of this invention the term "supercritical fluid" also includes such "near-critical fluids," where the fluid is either at or below the critical temperature and the properties begin to approach those of a supercritical fluid. For the purposes of this invention, a "near-critical fluid" is considered to exist at those conditions where the fluid is at temperatures from about 75% of the critical temperature to about 100% of the critical temperature, and at pressures from about 25% of the critical pressure to about 100% of the critical pressure.

One can visually observe the phase behavior of the reaction mixture by conducting the reaction in a vessel equipped with a transparent window, or by simulating the reaction mixture with a solution of similar concentration in such a vessel. Systematic determination of the phase boundaries of the reaction mixture can be determined by standard techniques using such a vessel that is also equipped with a means of varying the vessel volume at fixed composition and temperature. The vessel is loaded with the various components at the specified composition of the reaction mixture, heated to the reaction temperature, then the solution pressure is varied by changing the vessel volume until a phase transition is visually observed. After measuring the phase boundary of a solution of interest over the range of anticipated compositions, one can define the operating conditions necessary to achieve the supercritical or near-critical state for conducting the desired reaction.

Any suitable SCF solvent may be used in the process of this invention, including, but not limited to, carbon dioxide, nitrous oxide, sulfur hexafluoride, fluoromethane, trifluoromethane, tetrafluoromethane, ethane, ethylene, propane, propanol, isopropanol, propylene, butane, butanol, isobutane, isobutene, pentane, hexane, cyclohexane, benzene, toluene, o-xylene, water, and mixtures thereof, provided that it is inert to all reagents and products. Preferred SCF solvents include carbon dioxide or a C1–C6 alkane, optionally substituted with Cl, F or Br. More preferred supercritical fluids are carbon dioxide, trifluoromethane, pentane, and propane.

Separation and/or purification of the desired products, including MBL or MeMBL, from unreacted starting lactone and/or reaction byproducts may be performed by processes known in the art. A particularly suitable method to recover the desired product is to polymerize MBL in GBL solution, or MeMBL in GVL solution, using standard free-radical polymerization, isolate the polymer by precipitation, and then thermally depolymerize back to MBL or MeMBL, as the case may be, by heating under vacuum. Finally, MBL can be separated from GBL by melt crystallization. Another effective method is liquid-liquid extraction.

Non-limiting reactors suitable for the process of the instant invention include tubular, fluidized bed, fixed bed, trickle bed, transport bed, and stirred tank reactors. The process can be run in either batch or continuous mode as described, for example, in H. Scott Fogler, *Elements of Chemical Reaction Engineering*, $2^{nd}$ Edition, Prentice-Hall Inc, CA, 1992. The process can also be run in either a single homogeneous phase over the solid catalyst, or the reactants and SCF may be in two different phases over the solid catalyst.

The catalysts of the present invention can be made by (or are obtainable by) a method as follows.

Porous silica powder, such as the material sold by Grace Davison, Inc. (Columbia, Md.) with a pore volume of at least 0.4 cc/g attributable to pores having a diameter between 65 and 3200 Angstroms is used as a catalyst matrix. Porosity preferably is determined by mercury porosimetry. Preferably the porous silica contains compounds of aluminum, titanium and/or zirconium. These latter silicas are preferred because of their hydrothermal stability.

A suitable way of choosing appropriate starting porous silica is to eliminate first those silicas that have a mean pore diameter less than 65 Angstroms and porosity less than 0.4 cc/g attributable to pores having diameters between 65 and 3200 Angstroms. Next, a porous silica manufacturer that describes its products in terms of mean pore diameter can be consulted to see if the manufacturer has the underlying data from which the mean pore diameter was calculated. If so, the manufacturer may be able to specify which, if any, of its products have pore volumes of greater than 0.4 Angstroms attributable to pores having diameters between 65 and 3200 Angstroms. These materials preferably should be independently tested by mercury porosimetry to determine that they meet the porosity characteristics required by this invention.

Organic compounds such as the carboxylates, such as acetate, propionate, butyrate, and 2-ethylhexanoate of a catalytic element selected from the group consisting of potassium, cesium and rubidium is dissolved in aqueous or non-aqueous solvent and contacted with the porous silica. Organic compounds do not include carbonates of the aforesaid catalytic elements. Organic compounds containing acetates are preferred. Other organic anions such as acetylacetonates can be used. One convenient method for introducing the catalytic element into the porous silica is to dissolve a suitable weight of the organic compound of the catalytic element in just enough solvent to equal the volume of the pores of the selected amount of the porous silica. The amount of organic compound should be chosen to provide to the silica from 0.1 wt % to 40 wt % of the element relative to the combined weight of the porous silica plus the element (as opposed to the compound of which the element is a part). The resulting material is allowed to dry, preferably in a nitrogen environment for an extended time. The purpose of the drying is to remove at least a portion of the solvent in which the organic compound is dissolved.

Organic compounds such as the alkoxides can also be used. Organic alkoxides of an element selected from the group consisting of potassium, cesium, and rubidium can contain from one to 20 carbon atoms and preferably 1 to 5 carbon atoms in the alkoxide group. The organic alkoxide should be soluble in the solvent. Most alkoxides can be dissolved in non-aqueous solutions such as ethanol, propanol, or isopropyl alcohol. Subsequent methods for introducing the element and drying are the same.

The dried material is then heated (for example in an alumina boat placed in a tube furnace) at an ambient temperature of 350° C. to 550° C. (The temperature of the catalyst material may be somewhat higher because of exothermic reactions taking place on the material.) A temperature between 450° C. and 550° C. is preferred. Either during the heating or subsequent to it, but at the same temperature, the material is flushed with an oxygen-containing gas (e.g. air), which is believed to burn off organic residues formed during the heating step. In a tube furnace, an airflow rate of at least 110 cc/min in a 3 cm diameter tube furnace, which corresponds to a linear velocity of 15.6 cm/min was found to be acceptable. Use of sufficiently high airflow rates is important to produce a high surface area material. In a tube furnace, the material can be heated at a rate of 5° C./min to 120° C., and can be exposed to this temperature for 4 hours. It can be heated subsequently at a rate of 5° C./min to approximately 450° C. and held at this temperature for 16 hours. Other equipment can be used to perform the heating step. Such equipment includes fluidized bed and rotary calcination equipment.

Heating can be accomplished in air or in a combination of an inert gas such as nitrogen, argon, or krypton for parts of the cycle, followed by air. An initial drying step at 120° C. in nitrogen, another inert gas, or air is preferred for a period of 30 minutes to 24 hours. Following this drying step, the catalyst can be heated in air or nitrogen to a temperature of 350° C. to 550° C. For acetate precursors, 450° C. to 550° C. is required. Heating times can range from 30 minutes to 48 hours. The final heating step preferably is performed in air for at least 30 minutes.

Once the catalyst is made as described above, it can be tested to confirm that it has a pore volume of at least about 0.3 cc/g of catalyst attributable to pores having a diameter between about 65 and 3200 Angstroms. (The reason that the porosity of the starting porous silica decreases after treatment is believed to be attributable to the inclusion of the catalytic metal into the silica.)

Pore volume may be obtained by a variety of techniques, but preferred techniques are mercury (Hg) and nitrogen porosimetric techniques, with Hg porosimetry being most preferred.

Mercury porosimetry data can be obtained at 414 MPa using, for example, a Micromeritics 1 Model 9420 AutoPore III Instrument (Micromeritics Inc., One Micromeritics Drive, Norcross Ga. 30093-1877). This technique permits one to measure the pore volume and size by forcing mercury to penetrate inside the open porosity. Mercury is used because it behaves as a non-wetting liquid with a large number of materials.

Mercury is forced to enter into the pores by applying a controlled increasing pressure. As a sample holder is filled with mercury under vacuum conditions, mercury surrounds the sample without entering the pores due to the very low residual pressure. During the test, the pressure is increased, and the volume of mercury penetrated is detected by means of a capacitive system. The decreasing volume of mercury in the sample holder represents the pore volume. The penetration pressure is directly related to the pore access size by a well-known mathematical model, expressed by the Washburn equation:

$$D = -4\gamma \cos(\theta)/Pc$$

Where:
γ is surface tension of pure mercury (480 dyne/cm);
θ is contact angle between mercury and the solid (average value 140° C.);
Pc is mercury penetration equilibrated pressure; and
D is pore diameter.

The distribution of pore size, as well as the total porosity, bulk and apparent density and the specific pore volume can be obtained by the relationship between the pressure necessary for penetration (the pore dimension) and the volume of penetrated mercury (pore volume). At each pressure, therefore, a differential volume of Hg can be calculated which occupies the pores of the solid; this represents the additional Hg volume which is intruded as a consequence of a pressure increase. At lower applied pressure, larger pores are filled with Hg. With increasing applied pressure, smaller pores are occupied up to the smallest pore diameter reasonably measurable by this technique, 65 Angstroms. In this way, a distribution of pore sizes as a function of applied pressure can be obtained.

Pores are assumed to be of a cylindrical shape, as is standard for this technique.

Sample compressibility correction is calculated post priori by determining the volume of samples and pores not yet intruded as a function of applied pressure. The resulting relationship is used to correct the raw intrusion data for sample compression effects.

From the Washburn equation it is clear that the pore size range that can be investigated by mercury porosimetry is directly related to the pressure range.

Alternatively, nitrogen porosimetry may be used. Dinitrogen adsorption/desorption measurements can be performed at 77.3° K. using, for example, Micromeritics ASAP model 2400/2405 porosimeters. Samples can be degassed at 150° C. overnight prior to data collection. Pore volume distributions can be determined using a 27 point desorption isotherm and can be analyzed using the BJH method described in E. P. Barret, L. G. Joyner and P. P. Halenda, *J. Amer. Chem. Soc.*, 73, 373(1951).

In this invention, pores having diameters of 65 Angstroms up to 3200 Angstroms should contribute at least 0.3 cc/g pore volume to the final catalyst. Above 3200 Angstroms, inter-particle pores and void spaces are measured, and are not important for this invention.

If the catalyst possesses the correct porosity, it may be used as a precursor for grafting the zircomium, titanium or aluminum. If not, it may be necessary to repeat the catalyst synthesis using higher oxygen-containing gas flow rates than were used initially. The process may have to be repeated several times with successively higher gas flow rates until a catalyst with the correct porosity is finally obtained.

Onto these materials are added one or more inorganic alkoxides of aluminum, titanium or zirconium. The inorganic metal alkoxides used in this invention may include any alkoxide that contains from 1 to 20 carbon atoms and preferably 1 to 5 carbon atoms in the alkoxide group, and which preferably is soluble in the liquid reaction medium. Examples include, but are not limited to, zirconium n-propoxide and isopropoxide, titanium (IV) butoxide, aluminum isopropoxide and aluminum tri-sec-butoxide.

Inorganic alkoxides can be prepared in various ways. One method of preparation includes direct reaction of zero valent metals with alcohols in the presence of a catalyst. Many alkoxides can be formed by reaction of metal halides with alcohols. Also, alkoxy derivatives can be synthesized by the reaction of the alkoxide with alcohol in a ligand interchange reaction. Direct reactions of metal dialkylamides with alcohol also form alkoxide derivatives. Additional methods for preparing alkoxides are disclosed in "Metal Alkoxides" by D. C. Bradley et al., Academic Press, (1978).

The solvent media used in the process generally should be a solvent for the inorganic alkoxide or alkoxides, which can dissolve the alkoxide. While not wishing to be bound to any theory, it is believed that the alkoxide solutions, when contacting the catalyst candidate of step (f) will react with the hydroxyl groups on the surface of the catalyst candidate and associated water. Hence, direct covalent bonds can be formed between the alkoxy species and the catalyst surface.

The grafted material is then heated (for example in an alumina boat placed in a tube furnace) at an ambient temperature of 350° C. to 550° C. (The temperature of the catalyst material may be somewhat higher because of exothermic reactions taking place on the material.) A temperature between 450° C. and 550° C. is preferred. Either during the heating or subsequent to it, but at the same temperature, the material is flushed with an oxygen-containing gas (e.g. air), which is believed to burn off organic residues formed during the heating step. In a tube furnace, an airflow rate of at least 110 cc/min in a 3 cm diameter tube furnace, which corresponds to a linear velocity of 15.6 cm/sec was found to be acceptable. Use of sufficiently high airflow rates is important to produce a high surface area material. In a tube furnace, the material can be heated at a rate of 5° C./min to 120° C., and can be exposed to this temperature for 4 hours. It can be heated subsequently at a rate of 5° C./min to approximately 450° C. and held at this temperature for 16 hours. Other equipment can be used to perform the heating step. Such equipment includes fluidized bed and rotary calcination equipment.

Heating can be accomplished in air or in a combination of an inert gas such as nitrogen, argon, or krypton for parts of the cycle, followed by air. An initial drying step at 120° C. in nitrogen, another inert gas, or air is preferred for a period of 30 minutes to 24 hours. Following this drying step, the catalyst can be heated in air or nitrogen to a temperature of 350° C. to 550° C. For acetate precursors, 450° C. to 550° C. is required. Heating times can range from 30 minutes to 48 hours. The final heating step preferably is performed in air for at least 30 minutes.

EXAMPLES OF THE INVENTION

Catalyst 1:

About 20 g of $SiO_2$ powder, Davicat 1415 (Grace Davison, Inc., Columbia, Md.) having a pore volume of approximately 0.85 cc/g was used. 8.45 g of rubidium acetate (Aldrich Chemical Co.) was dissolved in enough water to match the pore volume of the support. The amount of water used was approximately 17.0 $cm^3$. The material was allowed to dry for at least 12 hours in a nitrogen environment. Approximately 10 $cm^3$ of the material was loaded into an alumina boat and heated in a tube furnace. The internal diameter of the tube furnace was 10 cm. The airflow rate was greater than 1220 $cm^3$/min, which corresponds to a linear velocity of greater than 15.6 cm/min. Use of this higher airflow is important to produce a high surface area material. The material was heated at a rate of 5° C./min to 120° C., and was exposed to this temperature for 4 hours. It was subsequently heated at a rate of 5° C./min to approximately 450° C. (as measured by a thermocouple placed approximately 0.5 cm over the catalyst bed) and was held at this temperature for 16 hours.

After cooling to room temperature, 2.5 g of aluminum tri-sec butoxide (Aldrich, 20,107-3) was dissolved in 5 ml of isopropyl alcohol (EM Science) and allowed to contact about 5 g of the material, produced above, on a fritted funnel. An additional 10 ml of isopropyl alcohol was added to this mixture, which formed a gel. The excess alkoxide and alcohol was filtered off the material. The material was washed with an additional 50 ml of isopropyl alcohol.

The material was loaded into an alumina boat and heated in a tube furnace. The internal diameter of the tube furnace was 10 cm. The airflow rate was greater than 1220 $cm^3$/min, which corresponds to a linear velocity of greater than 15.6 cm/min. Use of this higher airflow is important to produce a high surface area material. The material was heated at a rate of 2.5° C./min to 120° C., and was exposed to this temperature for 1 hour. It was subsequently heated at a rate of 5.0° C./min to approximately 450° C. (as measured by a thermocouple placed approximately 0.5 cm over the catalyst bed) and was held at this temperature for 2 hours. The material was allowed to cool to room temperature in air.

Catalyst 2:

About 20 g of $SiO_2$ powder, Davicat 1415 (Grace Davison, Inc., Columbia, Md.) having a pore volume of approximately 0.85 cc/g was used. 8.45 g of rubidium acetate (Aldrich Chemical Co.) was dissolved in enough water to match the pore volume of the support. The amount of water used was approximately 17.0 $cm^3$. The material was allowed to dry for at least 12 hours in a nitrogen environment. Approximately 10 $cm^3$ of the material was loaded into an alumina boat and heated in a tube furnace. The internal diameter of the tube furnace was 10 cm. The airflow rate was greater than 1220 $cm^3$/min, which corresponds to a linear velocity of greater than 15.6 cm/min. Use of this higher airflow is important to produce a high surface area material. The material was heated at a rate of 5° C./min to 120° C., and was exposed to this temperature for 4 hours. It was subsequently heated at a rate of 5° C./min to approximately 450° C. (as measured by a thermocouple placed approximately 0.5 cm over the catalyst bed) and was held at this temperature for 16 hours and allowed to cool in air to room temperature.

3 g of zirconium isopropoxide (Alfa Aesar, 22989) was dissolved in 50 ml of isopropyl alcohol (EM Sciences, 42326) and stirred into 10 g of the material produced above.

The material was stirred for 1 hour and subsequently filtered on a fritted funnel. The powder was dried under nitrogen for 12 hours.

The material was heated at a rate of 5° C./min to 120° C., and was exposed to this temperature for 4 hours. It was subsequently heated at a rate of 5° C./min to approximately 450° C. (as measured by a thermocouple placed approximately 0.5 cm over the catalyst bed) and was held at this temperature for 16 hours and allowed to cool in air to room temperature.

The following examples were conducted in a continuous fixed bed reactor consisting of a 0.25-inch o.d.×0.049-inch wall×4.5-inch long 316 stainless steel tube packed with catalyst. The reactor was heated by cartridge-type electrical heaters mounted in an aluminum block enclosing the reactor. The lactone was combined with ethanol hemiacetal as the formaldehyde precursor and metered to the reactor as a liquid feed with a syringe pump. The ethanol hemiacetal was prepared by refluxing a 50 mol % paraformaldehyde solution in ethanol for four hours at 95° C. followed by cooling to room temperature and filtration. The carbon dioxide solvent was metered as a condensed liquid with a second positive-displacement pump, and the two streams were combined and heated prior to entering the reactor. Liquid-phase reactor effluent samples were collected downstream in an ice bath after venting the carbon dioxide, and reaction products were quantified by gas chromatography. The reactor pressure was controlled by a backpressure regulator located downstream of the reactor.

Example 1

The reactor was charged with 0.60 g of an Al-grafted 20% Rb/Davicat Si 1415 catalyst (Catalyst 1). The reactant feed solution consisted of 50.9 wt % GVL, 2.6 wt % diphenyl ether as an internal standard, and the balance was made up with the ethanol hemiacetal solution. This solution resulted in a 1.2:1 ratio of formaldehyde to GVL in the reactor feed, which was metered at a rate resulting in a weight hour space velocity (WHSV) in the reactor of 1.20 g GVL/(g catalyst-h). $CO_2$ was used as the SCF solvent phase, and the flow rate was metered independently to give a final total organic concentration of 4.0 mol % in the reactor feed. The reactor was operated at a temperature of 251° C. and a pressure of about 20.0 MPa. The cumulative turnover number for the reaction was 11.4 mol GVL converted/mol of catalyst, and the corresponding reaction profile showing conversion of GVL to MeMBL is summarized below:

| Run Time (h) | GVL Conversion (%) | MeMBL Selectivity (%) | Reactor Productivity (g MeMBL/g catalyst-h) |
|---|---|---|---|
| 0.98 | 43.3 | 96.5 | 0.56 |
| 1.98 | 58.8 | 96.9 | 0.76 |
| 2.50 | 62.1 | 97.4 | 0.81 |
| 3.00 | 64.6 | 96.9 | 0.84 |
| 3.52 | 65.8 | 97.3 | 0.86 |
| 4.00 | 65.7 | 97.1 | 0.86 |

Example 2

The reactor was charged with 0.62 g of a Zr-grafted 20% Rb/Davicat Si 1415 catalyst (Catalyst 3). The reactant feed solution consisted of 52.3 wt % GVL, with the balance made up with the ethanol hemiacetal solution. This solution resulted in a 1.2:1 ratio of formaldehyde to GVL in the reactor feed, which was metered at a rate resulting in a weight hour space velocity (WHSV) in the reactor of 1.17 g GVL/(g catalyst-h). $CO_2$ was used as the SCF solvent phase, and the flow rate was metered independently to give a final total organic concentration of 3.9 mol % in the reactor feed. The reactor was operated at a temperature of 245° C. and a pressure of about 23.5 MPa. The cumulative turnover number for the reaction was 17.6 mol GVL converted/mol of catalyst, and the corresponding reaction profile showing conversion of GVL to MeMBL is summarized below:

| Run Time (h) | GVL Conversion (%) | MeMBL Selectivity (%) | Reactor Productivity (g MeMBL/g catalyst-h) |
|---|---|---|---|
| 0.58 | 86.7 | 97.7 | 1.11 |
| 1.10 | 74.3 | 98.1 | 0.96 |
| 2.18 | 67.4 | 98.1 | 0.87 |
| 3.18 | 66.2 | 98.0 | 0.85 |
| 4.18 | 51.5 | 96.8 | 0.65 |

The data of Examples 1 and 2 show that reactions done in accordance with the process of the present invention yield the desired products with adequate and relatively sustained GVL conversion and reactor productivity and with high selectivity. These examples show more sustained activity with adequate GVL conversion levels and higher reactor productivities with time on stream than the examples from US 2003-0166949 A1 that are illustrated in Table 1.

What is claimed is:

1. A process for preparing a reaction product comprising an alpha-methylene lactone of the Formula II, said process comprising combining a lactone of the Formula I with formaldehyde derived from a formaldehyde source and a solvent to produce a reaction mixture,

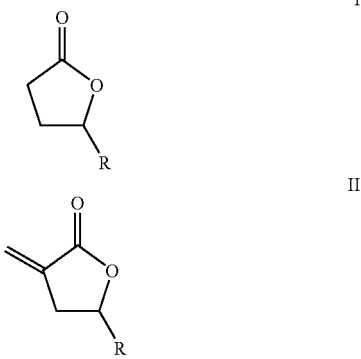

wherein R is selected from the group consisting of hydrogen, methyl, ethyl, and straight or branched $C_3$–$C_5$ alkyl;
at a temperature and pressure sufficient to cause the reaction mixture to exist as a supercritical or near-critical fluid, said temperature being sufficient to cause the formation of said alpha-methylene lactone of Formula II;
said reaction mixture being in the presence of a grafted catalyst;
said grafted catalyst made by a process comprising:
(a) contacting (i) porous silica, optionally containing a first element, said first element being one, two or three members selected from the group consisting of aluminum, zirconium, and titanium, said silica having a pore volume of at least 0.4 cc/g attributable to pores having pore diameters between 65 and 3200 Angstroms, with (ii) a solution comprising a solvent and an organic compound of a second element, said second element being one, two or three members selected from the group consisting of potassium, cesium and rubidium;

(b) drying the product of step (a) to remove at least a portion of said solvent;

(c) heating the product of step (b) to a temperature in the range of 350° C. to 550° C. to produce a catalyst precursor;

(d) flushing at a preselected flow rate an oxygen-containing gas over said catalyst precursor either during step (c), or after step (c) while the temperature is still in the range of 350° C. to 550° C. to produce a catalyst candidate in which the second element is present in said catalyst candidate in an amount from about 0.1% to about 40% by weight of the combined weight of the catalyst candidate and the second element;

(e) determining by porosimetry whether said catalyst candidate has a pore volume of at least about 0.3 cubic centimeters per gram of catalyst attributable to pores having a diameter between 65 and 3200 Angstroms; and (f) if said catalyst candidate does not have a pore volume of at least about 0.3 cubic centimeters per gram of catalyst attributable to pores having a diameter between 65 and 3200 Angstroms, repeating, optionally more than once, steps (a) through (e) using in step (d) flow rates successively greater than said preselected flow rate until the catalyst candidate has a pore volume of at least about 0.3 cubic centimeters per gram of catalyst attributable to pores having a diameter between 65 and 3200 Angstroms;

(g) contacting the material produced in step (f) with a second solution of zirconium, aluminum or titanium alkoxides dissolved in a second solvent, said alkoxides containing from one to 20 carbon atoms;

(h) filtering the material of step (g);

(i) drying the product of step (h) to remove at least a portion of said second solvent;

(j) heating the product of step (b) to a temperature in the range of 350° C. to 550° C.; and (k) flushing at a preselected flow rate an oxygen-containing gas over the product of step (j) either during step (j), or after step (j) while the temperature is still in the range of 350° C. to 550° C. to produce the grafted catalyst.

2. The process of claim 1 wherein the porosimetry is mercury porosimetry.

3. The process of claim 1 wherein R is hydrogen or methyl.

4. The process of claim 1 wherein the solvent is carbon dioxide or a $C_1$–$C_6$ alkane, optionally substituted with CL, F, or Br.

5. The process of claim 4 wherein the solvent is carbon dioxide, pentane, triflurormethane, or propane.

6. The process according to claim 1 wherein the formaldehyde is derived from a formaldehyde source selected from the group consisting of trioxane, anhydrous formaldehyde, formalin, formaldehyde oligomer, formaldehyde cyclic oligomer, formaldehyde acetal, formaldehyde hemiacetal, and formaldehyde polymer.

7. The process according to claim 6 wherein the formaldehyde source is formalin, trioxane, formaldehyde hemiacetal or paraformaldehyde.

8. The process of claim 1 wherein the temperature is in the range of from about 70° C. to about 400° C. and the pressure is in the range of from about 5 MPa to about 60 MPa.

9. The process of claim 1 further comprising separating said alpha methylene lactone from said reaction product.

* * * * *